United States Patent [19]

Coyle

[11] 4,059,598

[45] Nov. 22, 1977

[54] DECOMPOSITION OF HYDROPEROXIDES IN PROPYLENE EPOXIDATION REACTION PRODUCT

[75] Inventor: James J. Coyle, Houston, Tex.

[73] Assignee: Shell Oil Company, Houston, Tex.

[21] Appl. No.: 387,849

[22] Filed: Aug. 13, 1973

Related U.S. Application Data

[63] Continuation of Ser. No. 384,857, Aug. 2, 1973, abandoned, and a continuation-in-part of Ser. No. 102,971, Dec. 30, 1970, abandoned.

[51] Int. Cl.$^2$ .................. C07D 301/20; C07D 301/32
[52] U.S. Cl. .......................... 260/348.16; 260/348.29
[58] Field of Search .......................... 260/348.5 L, 348

[56] References Cited

U.S. PATENT DOCUMENTS

| | | | |
|---|---|---|---|
| 2,687,438 | 8/1954 | Lorand et al. | 260/618 C |
| 2,718,530 | 9/1955 | Conner | 260/618 C |
| 3,505,360 | 4/1970 | Allison et al. | 260/348.5 V |
| 3,557,182 | 1/1971 | Nagata | 260/464 |

FOREIGN PATENT DOCUMENTS

| | | |
|---|---|---|
| 1,505,921 | 1/1967 | France |
| 1,572,146 | 5/1969 | France |

OTHER PUBLICATIONS

Edwin S. Gould et al., Journal of Catalysis, vol. 13 (1969) pp. 238–244.

Primary Examiner—Norma S. Milestone
Attorney, Agent, or Firm—A. A. Jecminek

[57] ABSTRACT

In a reaction product of propylene epoxidation with an organic hydroperoxide in the presence of a heterogeneous catalyst, decomposition of residual hydroperoxides is effected by contact of the reaction product mixture at elevated temperature and pressure with a heterogeneous cobalt oxide catalyst which may also contain copper oxide as a promoter. The hydroperoxide is thereby decomposed to the corresponding alcohol without significant loss of propylene oxide or production of undesirable contaminants.

6 Claims, No Drawings

DECOMPOSITION OF HYDROPEROXIDES IN PROPYLENE EPOXIDATION REACTION PRODUCT

CROSS REFERENCES TO RELATED APPLICATIONS

This is a continuation of application Ser. No. 384,857, filed Aug. 2, 1973 now abandoned, and a continuation-in-part of application Ser. No. 102,971, filed Dec. 30, 1970, now abandoned. Related subject matter is claimed in copending application Ser. No. 387,850, filed Aug. 13, 1973, now abandoned.

BACKGROUND OF THE INVENTION

Several processes are known for reacting olefins with an organic hydroperoxide to produce oxirane compounds. For example, the process of Smith, U.S. Pat. No. 2,754,325, employs water soluble heteropoly acids containing the transition metals chromium, molybdenum or tungsten as homogeneous catalysts for the epoxidation of olefins in the presence of peroxides, which may be organic hydroperoxides, in an aqueous system. The use of solutions of transition metal compounds as homogeneous epoxidation catalysts is described in U.S. Pat. No. 3,350,422 and U.S. Pat. No. 3,351,635 of Kollar, which also provide a detailed description of the state of the art as of about 1966. Still another catalyst system useful for epoxidizing olefins is that described by deRoch et al. in U.S. Pat. No. 3,489,775, wherein the catalyst consists of salts of a nitrogenous organic base and an acid of molybdenum, tungsten or vanadium.

It is also known to employ heterogeneous catalyst to catalyze the epoxidation of an olefinically unsaturated material by reaction with an organic hydroperoxide.

All of these processes, while offering a distinct advantage over the older chlorohydrin process, suffer from the disadvantage that there is less than complete conversion of the organic hydroperoxide reactant. Consequently, the effluents from these epoxidation reactions (epoxidates) contain organic hydroperoxides. Hydroperoxides are known to decompose, thermally or in the presence of transition metal ions, into free radicals which, in turn, promote undesirable reactions in the subsequent processing of the epoxidates. For example, it has been found that thermal processing, as in distillation, of a propylene epoxidate which contains ethylbenzene and ethylbenzene hydroperoxide results in the formation of $C_5 - C_7$ hydrocarbons and similarly, a propylene epoxidate which contains propylene and t-butyl hydroperoxide results in the formation of undesired $C_7$ and other light hydrocarbons. Such hydrocarbons are highly undesirable contaminants since they are difficult to separate by conventional fractionation techniques.

More specifically, in recovering propylene oxide by distillation from an epoxidate derived from the epoxidation of propylene with ethylbenzene hydroperoxide in the presence of a hetergeneous catalyst, sizeable concentrations of $C_5 - C_7$ hydrocarbons, e.g., 2,000 ppm, remain in the propylene oxide product fraction. Such a product is generally considered unsuitable for commercial purposes. Since an analysis of the epoxidation reaction effluent typically shows less than 10 ppm of such contaminants, and since their concentration in the propylene oxide product cannot be explained on the basis of mere concentration effect, it is apparent that such hydrocarbon contaminants are formed during processing of the epoxidate in the downstream product recovery system.

Therefore, there is a need for a method of converting the unreacted organic hydroperoxides present in a propylene epoxidation reaction effluent into stable compounds in order to prevent, or at least minimize, the decomposition of the peroxides into free radicals with the consequent hydrocarbon formation. Such conversion is preferably conducted before such epoxidate is subjected to the successive fractionations of the product recovery system.

One solution to this problem is presented in U.S. Pat. No. 3,464,897 of Jubin wherein a process is disclosed for distilling an epoxidate in the presence of a suitable azeotroping agent, e.g., an open chain or cyclic paraffin containing from 8 to 12 carbon atoms. Such an azeotropic distillation effectively depresses the volatilities of the $C_5 - C_7$ hydrocarbons, thus permitting the recovery of substantially pure propylene oxide. However, such an approach is expensive and presents an additional problem in recovering the azeotroping agent from the extracted hydrocarbons.

Numerous acidic catalysts or soluble metal catalysts have been disclosed for the decomposition of organic hydroperoxides or their conversion into other compounds. Typically the catalysts or reactants employed are acids or ionized metal compounds in solution. The mechanism for acid and ionized metal-induced decompositions of hydroperoxides is discussed in Tobolsky et al, "Organic Peroxides," New York: Interscience, 1954, pp. 57–122 and Davies, "Organic Peroxides," London: Butterworths, 1961, pp. 174–192.

It has also been taught that metals and compounds of metals of Groups IV-A, V-A, or VI-A of the Periodic Chart, with the exception of chromium, catalyze the conversion of alkenyl hydroperoxides to epoxy alcohols (Allison et al, U.S. Pat. No. 3,505,360, issued Apr. 7, 1970).

The use of acidic or soluble metal catalysts of the prior art to effect decomposition of residual organic hydroperoxide present in the effluent from a propylene epoxidation reactor would result in undesirable reactions which adversely affect the yields and the economics of the process. Usually, the organic hydroperoxide will be present in only minor concentrations, the major constituents of the mixture comprising propylene, propylene oxide, alcohols, carbonyl compounds, the hydrocarbon precursor of the hydroperoxide, and the like. The use of acidic or soluble metal compounds as catalysts effect the transformation of the propylene oxide into glycols, and aid in the formation of various epoxide adducts, and may induce the polymerization of propylene to heavy ends of little commercial value.

Thus, a real need exists for a method by which organic hydroperoxides present in a mixture of propylene, propylene oxide, alcohols, carbonyl compounds, hydrocarbons, and the like found in a propylene epoxidation effluent may be effectively decomposed without inducing reactions or decompositions of the admixed organic compounds.

BRIEF SUMMARY OF THE INVENTION

According to the present invention, an epoxidate derived by reaction of propylene with an organic hydroperoxide in the presence of a heterogeneous catalyst is rendered stable toward hydrocarbon formation by contacting said epoxidate with a heterogeneous cobalt oxide catalyst, thereby to convert the organic hydroperoxides to stable compounds. The cobalt oxide catalyst may be promoted by the addition of copper oxide and, optionally, may be deposited on an inert inorganic support.

PREFERRED EMBODIMENTS OF THE INVENTION

The improved process of the invention is conducted by contacting an epoxidate which is the effluent from propylene epoxidation by means of an organic hydroperoxide, and which contains unreacted hydroperoxide, in the liquid phase with the catalyst composition described herein whereby the organic hydroperoxide is decomposed with minimal formation of $C_5$ - $C_7$ hydrocarbon by-product and minimal loss of epoxide, i.e., without substantial decomposition of propylene oxide. For example, in the epoxidation of propylene with ethylbenzene hydroperoxide in the presence of a heterogeneous catalyst there is produced a reaction product (epoxidate) containing, inter alia, unreacted ethylbenzene hydroperoxide and propylene oxide. In the downstream recovery system for recovering the propylene oxide, the presence of the unreacted ethylbenzene hydroperoxide causes several difficulties. Subjecting the epoxidate to the process of the instant invention destroys the hydroperoxide and thereby avoids these difficulties. Ethylbenzene hydroperoxide, a secondary hydroperoxide, is converted to a mixture of acetophenone and alpha-methylbenzyl alcohol. Whenever a tertiary hydroperoxide is employed in the process of this invention, the conversion product is the corresponding alcohol.

The efficiency of the process of this invention for the decomposition of organic hydroperoxides is a result of the ability of the heterogeneous cobalt oxide catalyst to selectively or preferentially decompose the organic hydroperoxides to innocuous byproducts without substantial conversion of the oxirane product present in a typical epoxidate. This selectivity with respect to conversion or decomposition of the organic hydroperoxide is illustrated by comparing the ratio of the pseudo first order decomposition rate constants for the hydroperoxide and the oxirane compound. The higher the ratio of these rate constants, the more selective is the process for decomposing the hydroperoxide. The data presented in Example 1 demonstrate that the catalyst systems of the instant invention are selective in decomposing organic hydroperoxides in admixture with oxirane compounds.

THE ORGANIC HYDROPEROXIDE

The method of the present invention is suitable for decomposing a wide variety of organic hydroperoxides which are employed as epoxidation agents. In particular, the process is useful in the decomposition of hydrocarbon secondary and tertiary hydroperoxides of from 3 to 20 carbon atoms per molecule which are free of olefinic unsaturation. Illustrative hydrocarbon hydroperoxides include tertiary alkyl hydroperoxides, such as tertiary butyl hydroperoxide and tertiary amyl hydroperoxide, and secondary and tertiary aralkyl hydroperoxides wherein the hydroperoxy group is a substituent on a carbon atom attached directly to an aromatic ring, such as ethylbenzene hydroperoxide, cumene hydroperoxide and tetralin hydroperoxide.

THE CATALYST

The catalyst compositions which are useful in the process of this invention are the oxides of cobalt, which optionally may be promoted by the inclusion therewith of oxides of copper. Representative cobalt oxides include cobaltous oxide, CoO; cobaltic oxide, $Co_2O_3$; and tricobalt tetraoxide, $Co_3O_4$. Suitable copper oxides which are useful as catalyst promoters, whenever a promoter is employed, include copper suboxide, $Cu_4O$; cuprous oxide, $Cu_2O$; and cupric oxide, CuO. Copper may be present in the range from 0 to 100% by weight of copper oxide based on the amount of cobalt oxide present.

The cobalt, and copper when employed, are present in the catalyst in the form of oxides. The catalyst may be prepared, if desired, from cobalt and copper compounds which are readily converted to the oxide, e.g., the corresponding metal carbonates. For example, the metal(s) may be precipitated from a solution of the nitrate(s) in the form of one or more compounds readily convertible to the oxide(s). Thus, the nitrate(s) may be combined with a solution of a carbonate to precipitate the metal(s) as carbonate(s). The precipitate thus obtained is a mixture of carbonate(s), basic carbonate(s), and hydroxide(s). It is collected, washed substantially free of electrolytes, then dried and calcined at a temperature of from about 200° C to about 400° C, a temperature of from about 250° C to about 300° C being preferred. The calcined material is used as a powder or is formed by, for example, pelleting under pressure using graphite as a lubricant.

It is generally preferable to employ the catalyst on an inert, neutral support. Among the wide variety of suitable inert, non-acidic, inorganic supports which may be employed are: carbonaceous materials such as charcoal; normally insoluble inorganic salts such as barium sulfate; and non-acidic crystalline aluminum silicates of the type known in the art as molecular sieves. Preferred inert, non-acidic, inorganic supports are inorganic oxides based on aluminum and/or silicon. Illustrative of such preferred supports are the aluminas, including calcined and sintered varieties, gels, hydrates, bauxites and corundums; micas; spinels; silicas; including gels, quartz, and silicates; kieselguhr; clays, including kaolins, serpentine minerals, bentonites, montmorillonites, and illites. Combinations of the above-indicated aluminum- or silicon-based supports, compounded by known methods of catalyst preparation, are also suitably employed, provided care is taken to avoid those having acidic properties. Kieselguhr is a particularly preferred support for the metal oxide(s).

The surface area of the catalystic composition can vary widely and generally lies within the range of from about 10 to 800 m²/g. Preferred catalyst compositions have surface areas of from about 25 to about 200 m²/g.

THE PROCESS CONDITIONS

The method of the present invention is especially adapted to decompose organic hydroperoxides present in the effluent from a propylene epoxidation reaction.

Effluent from a reactor in which propylene is converted to propylene oxide by reaction with a hydroperoxide, which effluent is the typical feedstock for the hydroperoxide decomposition reaction of this invention, generally contains the following components: unreacted propylene, unreacted hydroperoxide, propylene oxide, alcohols, carbonyl compounds and the hydrocarbon analog of the hydroperoxides.

The decomposition of peroxy compounds according to this invention is generally effected in the liquid phase. It may be accomplished by passing the mixture through a suitably contained fixed bed of catalytic composite or by contacting the reaction mixture with slurried catalyst.

In practice, it has been found that best results are achieved when the decomposition takes place at moderate temperatures and pressures. Suitable reaction temperatures vary from about 0° C to about 200° C, and preferably from about 50° C to about 170° C. The reaction pressure is not critical and can vary from about 1 to about 100 atmospheres, provided it is sufficient to maintain the reaction mixture in liquid phase. The duration of contact between hydroperoxide-containing mixture and catalytic composite, expressed in terms of space velocity, likewise is not critical, and may vary between about 2 and about 50 hr$^{-1}$.

After the hydroperoxide-containing mixture has been treated by the method of the invention, the resultant stream, essentially free of hydroperoxides, is separated to recover the various components thereof. Conventional methods, such as fractional distillation, selective extraction, filtration, and the like may be used, depending upon the type and amount of admixed components.

In the examples which follow, the method of the present invention is illustrated by data showing the decomposition of ethylbenzene hydroperoxide in an ethylbenzene hydroperoxide/propylene oxide-containing mixture. In some of the examples the mixture was an actual epoxidate produced by reaction of propylene with ethylbenzene hydroperoxide in the presence of a heterogeneous catalyst. In other examples the mixture was synthetically produced by combining ethylbenzene hydroperoxide and propylene oxide with other compounds typically present in an epoxidation reaction effluent as described above. The examples are illustrative only and are not to be construed as restricting the present invention to such components or to such a reaction system.

EXAMPLE 1

A number of metal oxide compositions (as specified in Table 1) were screened for effectiveness in treating a synthetically formed mixture resembling an epoxidate containing, inter alia, ethylbenzene hydroperoxide and propylene oxide, to decompose the ethylbenzene hydroperoxide without significant decomposition of the propylene oxide.

The synthetic epoxidate contained 1.24% wt acetophenone, 14.2% wt propylene oxide, 17.33% wt α-methylbenzyl alcohol, 9.05% wt ethylbenzene hydroperoxide and 58.2% wt ethylbenzene.

A series of experiments were made in which 100 mg portions of various metal oxide catalyst compositions and 10 ml of this synthetic epoxidate were sealed in 20 ml glass ampoules and maintained in a shaker oil bath at 100° C for various periods of time. At the end of the period, the contents of the ampoules were analyzed by gas-liquid chromatography (GLC) to determine the concentrations of each of components listed above.

From these data, pseudo-first order decomposition rate constants, corrected for thermally induced decomposition, were calculated for the hydroperoxide ($K_{ROOH}$) and for the epoxide ($K_{PO}$).

Also calculated were the ratios of the first order decomposition rate constant of the hydroperoxide to that of the epoxide ($K_{ROOH}/K_{PO}$). This ratio is a measure of the effectiveness of a given catalytic composition in selectively decomposing the hydroperoxide, i.e., decomposing the hydroperoxide without decomposing a significant proportion of the epoxide present. The higher this ratio, the more selective is the given catalytic composition.

Data from these experiments are tabulated in Table 2.

The metal oxide compositions listed in Table 1 are commercially available catalyst compositions which were manufactured, respectively, by Harshaw Chemical Company and Girdler for use in various metal oxide catalyzed reactions. The characterizing information is that given by the supplier. The composition designations in the first column of each table are supplied by applicant. In each case, the designation indicates the metals present. Where several compositions have the same metal, they are arranged in numerical order by decreasing amounts of metal content and are grouped by type of support in the order of Kieselguhr, alumina and silica.

It was concluded from a study of the experiments that the length of reaction time appeared to influence the ratio of $K_{ROOH}/K_{PO}$. Accordingly, the data in Table 2 are grouped by increasing run lengths. For a given run length the data are arranged by increasing $K_{ROOH}/K_{PO}$ ratio.

Illustrative of effect of run length, as shown in Table 2, are the ratios for catalyst G-Co-1, in which the ratio of $K_{ROOH}/K_{PO}$ is 32 for a 2-hour run and greater than 60 for a 6-hour run, catalyst H-Co-2, in which the ratio is 21 for a 2-hour run and greater than 78 for a 13-hour run, and catalyst H-Co-1, in which the ratio is 56 for a 2-hour run and greater than 127 for a 13-hour run.

It will be noted that a number of the catalysts listed in Table 1 and illustrated by data in Table 2 are not within the scope of the invention as described and claimed herein. This refers particularly to those catalysts in which the active metal is chromium rather than cobalt. While it is shown by data in Table 2 that supported chromia catalysts are as effective, and in some cases superior, to most of the cobalt oxide catalysts under the conditions of this example, it was observed in a limited experiment comprising a continuous run for a long period of time that a supported chromia catalyst resulted in greater production of undesired hydrocarbon by-product than was obtained with supported cobalt oxide catalysts in similar runs. To facilitate consideration of each of these types of catalyst on their separate merits, the use of chromia catalysts is claimed in a separate continuation-in-part of Ser. No. 102,971, the parent of the present application.

Table 1

CATALYSTS

| Composition Designation[a] | Supplier's Designation | % Metal in Composition as Oxide(s)[b] | Inert Support | Commercial Form |
|---|---|---|---|---|
| H-Co-1 | Co-0108 | 39 | Kieselguhr | Tablet |
| H-Co-2 | Co-0101 | 35 | Kieselguhr | Tablet |
| H-Co-3 | Co-0502 | 18 | Alumina | Tablet |

Table 1-continued

CATALYSTS

| | | | | |
|---|---|---|---|---|
| H-Co-4 | Co-0501 | 10 | Alumina | Tablet |
| H-Co-5 | Co-0301 | 10 | Alumina | Extrudate |
| H-Co-6 | Co-T-303 | 3 | Coated Alumina | — |
| H-Co-7 | Co-0403 | 20 | Silica | Granules |
| H-Co-8 | Co-0401 | 13 | Silica | Granules |
| H-CoCu | Co-0901 | 5/5 | Alumina | Tablet |
| H-CoMo-1 | CoMo-0401 | 3/9 | Alumina | Tablet |
| H-Cr-1 | Cr-0304 | 33 | Alumina | Tablet |
| H-Cr-2 | Cr-1404 | 19 | Alumina | Tablet |
| H-CrMg | Cr-0101 | 12/2 | Alumina | Tablet |
| H-CrK | Cr-0105 | 9/1.5 | Alumina | Tablet |
| G-Co-1 | G-61RS | 62 | Kieselguhr | Tablet |
| G-Co-2 | G-61 | 62 | Kieselguhr | Tablet |
| G-Co-2r | G-67 | — | Kieselguhr | Tablet |
| G-Co-3 | T-1640 | 16.3 | Silica | Spheres |
| G-Co-4 | T-1641 | 25 | Silica | Spheres |
| G-Co-5 | G-62 | 33 | Refractory Oxide | Tablet |

| Size | Apparent Packed Bulk Density lbs/ft³ | Surface Area, m²/gm | Pore Volume, cc/gm | Remarks |
|---|---|---|---|---|
| 3/16" | 70 | 140 | .40 | |
| 3/16" | 71 | 130 | .35 | |
| ⅛" | 77 | 49 | .38 | |
| ⅛" | 60 | 60 | .51 | |
| 3/16" | 75 | 6.8 | .07 | |
| — | — | 175 | — | |
| 4–8 mesh | 30 | 6 | .38 | |
| 4–8 mesh | 30 | 1 | .36 | |
| ⅛" | 67 | 59 | .29 | "Activated alumina" |
| ⅛" | 60 | 160 | .40 | Support is "Silica promoted" |
| ⅛" | 73.5 | 120 | .26 | Alumina is "silicated" |
| ⅛" | 72 | 80–100 | .38 | "High activity alumina" |
| ⅛" | 62 | 45 | .31 | |
| ⅛" | 67.5 | 67 | .34 | "Activated alumina" |
| 3/16" × ⅛" | — | — | — | |
| 3/16" × ⅛" | — | — | — | |
| 3/16" × ⅛" | — | — | — | "Zr promoted cobalt" |
| ¼" – 1/5" | — | 110 | — | |
| ¼" – 1/5" | — | 82 | — | |
| ¼" × ¼" | — | 40 | — | "Reduced and stabilized metal oxide" |

[a] Prefix H indicates that composition supplied by Harshaw. Prefix G indicates that composition supplied by Girdler. Letters following prefix indicate metals whose oxides are present.
[b] Where two metals present, concentration shown in order of "Designation".

Table 2

BATCH DECOMPOSITION OF HYDROPEROXIDE

| Composition Designation | Run | Metal | % | Support |
|---|---|---|---|---|
| H-Co-2 | 1461 | Co | 35 | Kg[a] |
| G-Co-1 | 1463 | Co | 62 | Kg |
| H-Co-1 | 1462 | Co | 39 | Kg |
| H-Co-4 | 1472 | Co | 10 | Al[b] |
| H-Co-3 | 1473 | Co | 18 | Al |
| H-Co-6 | 1567 | Co | ~3 | Coated Al |
| G-Co-2 | 1471 | Co | 62 | Kg |
| G-Co-4 | 1563 | Co | 25 | Si[c] |
| H-CoMo-1 | 1641 | Co/Mo | 3/9 | Al (Silicon Promoted) |
| G-Co-3 | 1566 | Co | 16.3 | Si |
| G-Co-5 | 1564 | Co | 33 | Refractory oxide |
| G-CoZr | 1562 | Co/Zr | | Kg |
| H-Cr-1 | 1644 | Cr | 33 | Al |
| H-CrMg | 1645 | Cr/Mg | 12/2 | Al |
| H-Cr-2 | 1647 | Cr | 19 | Al |
| H-CrK | 1646 | Cr/K | 9/1.5 | Al |
| H-CoCu | 1643 | Co/Cu | 5/5 | Al |
| H-Co-8 | 1454 | Co | 13 | Si |
| H-Co-7 | 1456 | Co | 20 | Si |
| G-Co-1 | 1435 | Co | 62 | Kg |
| H-Co-5 | 1453 | Co | 10 | Al |
| H-Co-2 | 1455 | Co | 35 | Kg |
| H-Co-1 | 1452 | Co | 39 | Kg |

| $K_{PO}$ Hr⁻¹ (×10⁻³) | $K_{ROOH}$ Hr⁻¹ ×10⁻³ | $K_{ROOH}/K_{PO}$ | | | |
|---|---|---|---|---|---|
| | | 2 hr | 4 hr | 6 hr | 13 hr |
| 12.8 | 265 | 21 | | | |
| 19.6 | 620 | 32 | | | |
| 9.9 | 545 | 56 | | | |
| 11.9 | 51 | | 4 | | |
| 3.55 | 48 | | 14 | | |
| 18.3 | 250 | | 14 | | |
| 3.55 | 185 | | 52 | | |
| 2.8 | 7.8 | | | | 2.8 |
| 41.8 | 175 | | | | 4.2 |
| 4.08 | 23.2 | | | | 5.7 |
| 2.95 | 28.9 | | | | 10 |
| 14.4 | 152 | | | | 11 |
| 14.4 | ≧881 | | | | ≧61 |
| 12.6 | 807 | | | | 64 |
| 9.82 | ≧881 | | | | 90 |
| 4.0 | ≧881 | | | | ≧220 |
| 2.55 | ≧881 | | | | ≧345 |
| 3.76 | 9.46 | | | | 3 |
| .994 | 5.43 | | | | 6 |
| 8.71 | >520 | | | | >60 |
| .077 | 4.85 | | | | 63 |
| 6.7 | >520 | | | | >78 |
| 4.12 | >520 | | | | >127 |

[a] Kg = kieselguhr
[b] Al = alumina
[c] Si = silica

EXAMPLE 2

Three of the more effective catalytic compositions, as found in the experiments tabulated in Table 2, were employed to continuously decompose the hydroperoxide present in the effluent from a propylene epoxidation reactor. After varying periods of continuous service, the catalytic compositions were employed in batch experiments, at 100° C, to decompose the synthetic epoxidate of Example 1. As shown in Table 3, the ability of the catalytic compositions to preferentially decompose hydroperoxide significantly improves with usage.

EXAMPLE 3

Ethylbenzene hydroperoxide was fed to an epoxidation reactor wherein a major proportion (ca. 81%) was converted by reaction with propylene. The crude epoxidate, comprising propylene, propylene oxide, acetophenone, α-methylbenzyl alcohol, ethylbenzene, and ethylbenzene hydroperoxide was contacted with ground and screened 14/20 mesh Girdler G61RS catalytic composition at a liquid hourly space velocity of 12 hr$^{-1}$ and a temperature of 100° C. Analysis of the treated crude epoxidate indicated that approximately 99.7% of the ethylbenzene hydroperoxide fed to the epoxidation reactor had been decomposed. Molar selectivities, based on hydroperoxide consumed over the hydroperoxide decomposition catalyst, were approximately 68% to acetophenone and 32% to α-methylbenzyl alcohol. Small amounts of acetaldehyde and benzaldehyde were also detected. After 73 hours of operation, propylene oxide losses occasioned by contact of the crude epoxidate with the catalytic composition appeared to have stabilized at approximately 0.5% present in the epoxidation reactor effluent. Within the precision of analytical accuracy, the total $C_5$, $C_6$, and $C_7$ hydrocarbon contents of the treated crude epoxidate was less than 5 ppm.

EXAMPLE 4

Crude epoxidate containing various proportions of ethylbenzene hydroperoxide was continuously contacted at 100° C with various catalytic compositions, as shown in Table 4. In each case, the catalyst had been crushed to 8-30 mesh particules. For extended periods of time, at varying liquid hourly space velocities, treatment of the crude epoxidate by the method of the present invention resulted in near-quantitative decomposition of the contained hydroperoxide.

EXAMPLE 5

Ethylbenzene hydroperoxide was employed to epoxidize propylene to propylene oxide at two different conversion levels. A sample of each crude epoxidate was contacted with a catalytic composition at 96° C and the $C_{4-7}$ hydrocarbon concentration in the epoxidate after removal of most of the propylene was compared with the hydrocarbon content of untreated epoxidate. The beneficial effects of such treatment on minimizing hydrocarbon formation is indicated in Table 5.

Table 5

| Reduction in Epoxidation By-Product Formation by Catalytic Composition Treating | | | | |
|---|---|---|---|---|
| Run | V-1 | V-2 | V-3 | V-4 |
| Catalytic Composition | None | G-Co-1[a] | None | G-Co-1[a] |
| EBHP Concentration, %w Epoxidation Reactor Effluent | .23 | .23 | .79 | .79 |
| After Composition Contact | — | ~0 | — | ~0 |
| LHSV, Hr$^{-1}$, of Composition Contacting | — | ~12 | — | ~6 |
| $C_{4-7}$ Hydrocarbon Concentration, ppm (basis epoxide) | 568 | 246 | 1288 | 264 |

[a]8-35 mesh

Table 3

| BATCH DECOMPOSITION OF HYDROPEROXIDE WITH CATALYTIC COMPOSITIONS PREVIOUSLY EMPLOYED IN CONTINUOUS OPERATION | | | | | |
|---|---|---|---|---|---|
| Run | Catalytic Composition | Catalyst History[a] | $K_{PO}$ hr$^{-1}$ | $K_{ROOH}$ hr$^{-1}$ | $K_{ROOH}/K_{PO}$ |
| II-1a | H-Co-1 | Fresh (2 hr) | 9.9 × 10$^{-3}$ | .545 | 56 |
| II-1b | | Fresh (3 hr) | 4.12 × 10$^{-3}$ | >.52 | >127 |
| II-1c | | 60 hr cont. oper. (4 hr) | 2.36 × 10$^{-3}$ | 1.60 | 677 |
| II-2a | G-Co-1 | Fresh (2 hr) | 19.6 × 10$^{-3}$ | .62 | 32 |
| II-2b | | Fresh (13 hr) | 8.71 × 10$^{-3}$ | >.52 | >60 |
| II-2c | | 40 hr cont. oper. (4 hr) | 9.0 × 10$^{-3}$ | 1.52 | 168 |
| II-3a | G-Co-2 | Fresh (4 hr) | 3.55 × 10$^{-3}$ | .185 | 52 |
| II-3b | | 280 hr cont. oper. (4 hr) | 5.54 × 10$^{-3}$ | .91 | 164 |

[a]Batch reaction time indicated in parenthesis.

Table 4

| CONTINUOUS DECOMPOSITION OF HYDROPEROXIDE BY CATALYTIC COMPOSITION TREATING | | | | | | | |
|---|---|---|---|---|---|---|---|
| Run | IV-1 | | IV-2 | | IV-3 | | |
| Cat. Comp | H-Co-1 | | G-Co-1 | | G-Co-1 | | |
| LHSV, Hr$^{-1}$ | ~20 | | ~16 | | ~16 | | |
| Hrs. Continuous Operation | EBHP Concn., %w | | Hrs. Continuous Operation | EBHP Concn., %w | Hrs. Continuous Operation | EBHP (Concn., %w | |
| | In | Out | | In  Out | | In | Out |
| 2 | .79 | ~0. | 4 | 1.00  .44 | 6 | .99 | ~0. |
| 17 | 1.65 | ~0. | 33 | .67  ~0. | 108 | .95 | ~0. |
| 39 | .95 | ~0. | 81 | .46  ~0. | 139 | 1.38 | ~0. |
| 63 | 1.19 | .45 | 107 | 1.10  ~0. | | | |
| 77 | — | ~0. | 128 | 1.37  .08 | | | |

I claim as my invention:

1. A process for treating the reaction product of a process in which propylene is converted to propylene oxide by reaction with an organic hydroperoxide, said reaction product comprising propylene oxide and organic hydroperoxide, to decompose the organic hydroperoxide without substantial decomposition of the propylene oxide and without substantial formation of $C_5$ to $C_7$ hydrocarbons as products of the decomposition reaction, which comprises contacting a catalyst-free reaction mixture recovered as effluent from said epoxidation process, at a temperature in the range from about 0° to about 200° C and a pressure sufficient to maintain the reaction mixture in liquid phase with a non-acidic heterogeneous catalyst system consisting essentially of an oxide of cobalt on a solid support and from 0 to 100 percent by weight of copper oxide based on said cobalt oxide, and recovering a propylene oxide product essentially free of said organic hydroperoxide.

2. The method of claim 1 wherein the heterogeneous catalyst system is supported on an inert, inorganic support selected from the group consisting of aluminas, silicas, and kieselguhr.

3. The method of claim 2 wherein the organic hydroperoxide is selected from the group consisting of secondary and tertiary hydroperoxides of from 3 to 20 carbon atoms per molecule.

4. The method of claim 3 wherein the hydroperoxide is selected from the group consisting of tertiary butyl hydroperoxide, tertiary amyl hydroperoxide, ethylbenzene hydroperoxide, cumene hydroperoxide, and tetralin hydroperoxide.

5. The method of claim 1 wherein the contacting is effected at a temperature of from about 50° C to about 170° C, a pressure of from about 1 to about 100 atmospheres, and a liquid hourly space velocity from about 2 to about 50 $hr^{-1}$.

6. The method of claim 2 wherein the organic hydroperoxide is ethylbenzene hydroperoxide.

* * * * *